Jan. 8, 1963 D. L. ARMSTRONG Plant Pat. 2,213
PEACH TREE
Filed March 13, 1962
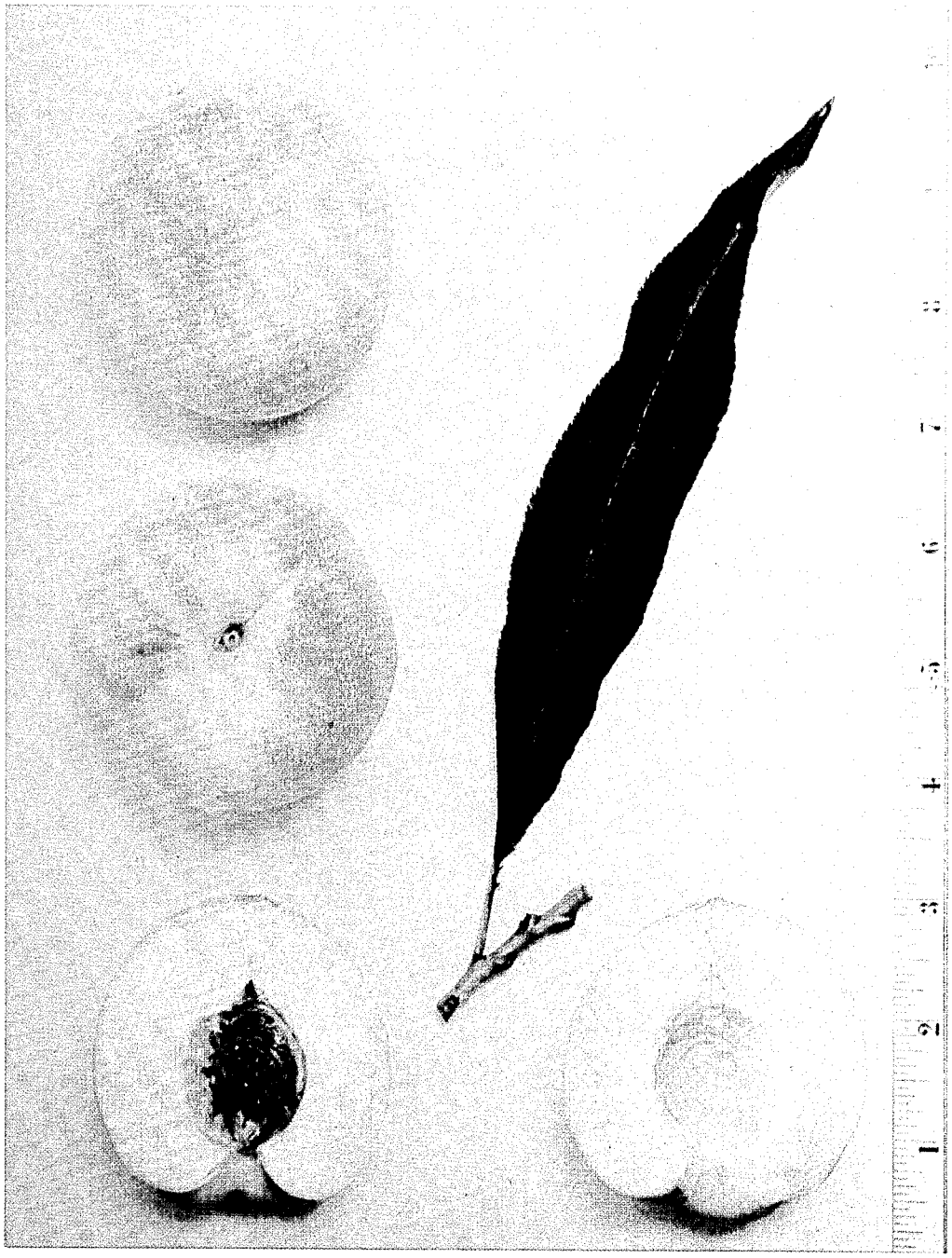
Inventor.
David L. Armstrong
By: Robb & Robb
Attorneys.

United States Patent Office

Plant Pat. 2,213
Patented Jan. 8, 1963

2,213
PEACH TREE

David L. Armstrong, Ontario, Calif., assignor to Armstrong Nurseries, Inc., Ontario, Calif., a corporation of California Filed Mar. 13, 1962, Ser. No. 179,503
1 Claim. (Cl. 47—62)

The present invention relates to a new and distinct variety of peach tree of the yellow-fleshed, freestone, fruiting, dwarf tree type, which was originated by me by crossing two unnamed and unpatented peach varieties derived from an extended series of crosses over four to six generations.

In the case of the unnamed seed parent, the ancestors were "Socala" peach (unpatented), "Coolidge Double Red" peach (unpatented), "Early Imperial" peach (unpatented),"Rio Oso Gem" peach (Plant Patent No. 84), "July Elberta" peach (Plant Patent No. 15), "Golden Blush" peach (Plant Patent No. 473), and "Chinese Dwarf" peach (unpatented). As the result of this breeding, the seed parent was characterized by a tree of normal or standard peach habit, combined with yellow-fleshed, freestone fruit of medium size, said fruit being fairly attractive and of reasonably good quality, and ripening in late July or early August in southern California. The flowers of this parent are double, showy and light pink in color.

In the case of the unnamed pollen parent, the ancestors were "Mayflower" peach (unpatented), "Babcock" peach (unpatented), "Rio Oso Gem" peach (Plant Patent No. 84), "Golden Blush" peach (Plant Patent No. 473), "Goldmine" nectarine (unpatented), "July Elberta" peach (Plant Patent No. 15) and "Chinese Dwarf" peach (unpatented). As the result of this breeding, the unnamed pollen parent was characterized by a tree of normal or standard peach habit, bearing yellow-fleshed, freestone fruit or fairly attractive appearance and of reasonably good quality, said fruit ripening from mid June to late June in southern California. The flowers of this parent variety are single in petalage, but showy and light pink in color.

The primary objective of the breeding of my new variety was to produce a new variety of peach tree having a dwarf tree habit, but which bears large, attractive, yellow-fleshed, freestone fruit of good eating quality. This objective was fully achieved, along with other desirable features, as evidence by the following unique combination of characteristics which are outstanding in the new variety and which distinguish it from its parents, as well as from all other varieties of which I am aware:

(1) A vigorous tree habit and compact, bushy, dwarf form, said tree being characterized by internodes of the stem averaging approximately ¼ inch in length, together with leaves of relatively normal or standard size and appearance for peaches, thereby giving the tree an attractive bushy and densely foliaged appearance, and said tree attaining a height of no more than about 5 or 6 feet at the age of 10 years, with little or no pruning;

(2) Showy semi-double pink flowers which give the tree a very attractive appearance when in bloom;

(3) A tree chilling requirement about equal to that of "Springtime" peach (Plant Patent No. 1,268);

(4) A habit of beginning to bear at a relatively early age, combined with a habit of bearing heavy crops generally under conditions which prevail in California;

(5) Yellow-fleshed, freeestone fruit of medium size, combined with good quality and flavor;

(6) Attractive, relatively uniform, nearly symmetrical fruit of nearly round shape;

(7) An attractive fruit skin color of light yellow general tonality, moderately flecked, blushed and occasionally streaked with red; and (8) A fruit ripening period in early June at Wasco, California, said ripening period averaging from a few days to a week after that of "June Gold" peach (Plant Patent No. 1,884).

In comparison with its pollen parent, the new variety essentially differs therefrom by a dwarf tree habit characterized by short internodes, as compared with the normal, long internode habit of this parent, with the new variety ripening from one to two weeks earlier than this parent, and having semi-double flowers instead of the characteristic single petalage flowers of this parent.

As compared with the seed parent, my new variety essentially differs therefrom by having a dwarf tree habit characterized by short internodes rather than the normal, long internode habit of this parent, and a fruit ripening period ranging from early to mid June, as distinguished from the late July to early August ripening period of this parent.

In comparison with the various ancestral varieties referred to in the foregoing, excepting for the variety "Chinese Dwarf" peach, the new variety essentially differs from them all by having a dwarf tree habit characterized by short internodes, instead of the normal, long internodes of the standard peach habit of the ancestral varieties, whereas in comparison with "Chinese Dwarf" peach, the new variety bears yellow-fleshed, freestone fruit of reasonably good eating quality, with the fruit ripening from early June to mid June, as distinguished from the white-fleshed, clingstone, barely edible fruit of the "Chinese Dwarf" peach variety which normally ripens in August.

The dwarf habit of the new variety is similar to that of "Flory Dwarf" peach (unpatented), but the fruit of the new variety is of medium size, yellow-fleshed, attractively blushed red, and good quality, with a ripening period of from early June to mid June, whereas the fruit of "Flory Dwarf" peach is small, white-fleshed with a rather greenish skin color, and of poor quality, and said fruit ripening in August. Also, the new variety has a chilling requirement about equal to that of "Springtime" peach, whereas that of "Flory Dwarf" peach is much higher. The new variety is still further characterized by pink flowers, in contract to the red flowers of "Flory Dwarf" peach.

Asexual reproduction of my new variety as performed by budding at Wasco, California, shows that the foregoing characteristics and distinctions come true to form and are established and transmitted through succeeding propagations.

The accompanying drawing shows typical specimens of the fruit, foliage and wood of my new variety, with both exterior and section views of the fruit being shown, and all views being depicted in color as nearly true as it is reasonably possible to make the same in a color illustration of this character.

The following is a detailed description of my new variety, as based upon observations of specimens grown at Wasco, California, with color terminology in accordance with Robert F. Wilson's Horticultural Color Chart (hereinafter abbreviated as "Wilson") and Ridgway's Color Standards and Nomenclature (hereinafter abbreviated as "Ridgway"), except where general color terms of ordinary dictionary significance are obvious:

*Tree*

Habit: Vigorous; upright-spreading; compact; bushy; dwarf; internodes of the stem average approximately ¼ inch long; leaves of relatively normal or standard size and appearance for peaches.

Chilling requirement: About equal to that of "Spring time" peach.

Fruit production: Under California conditions, trees bear heavy crops and begin to bear at a relatively early age for peaches.

Current growth:

*Surface texture.*—Smooth at first, with lenticels small and minute; with age, some larger, cracked, slightly raised lenticels appear toward the base of the more vigorous shoots.

*Color.*—Green or reddish on exposed surfaces at first, with lenticels appearing as small, nearly white dots, but all becoming more brown with age.

Two-year wood:

*Surface texture.*—Somewhat bumpy and rough effect from raised nodes and buds and their closeness together on the stem; otherwise, internodes generally are smooth, with some slightly raised lenticels and irregular, longitudinal striations.

*Color.*—Generally brown, but sometimes reddish brown.

Old wood:

*Surface texture.*—With increasing diameter of the stem, the bumpiness and rough effect from the nodes and buds becomes less after they are covered by the growth of the stem; becoming more smooth overall, with moderate number of raised lenticels and some small longitudinal fissures.

*Color.*—From grey to greyish brown or reddish brown on more exposed surfaces.

Leaves:

*Size.*—Length—from 6½ inches to 7½ inches. Width—from 1¼ inches to 1½ inches.

*Shape.*—Lanceolate; apex acuminate.

*Color (mature).*—Upper surface—near Forest Green, Plate XVII (Ridgway). Under surface—near Chromium Green, Plate XXXII (Ridgway).

*Petiole.*—Medium length; from medium thickness to thick.

*Margin.*—Finely serrate; glandular.

*Glands.*—Mixed globose and reniform; medium size; usually 3, but sometimes from 4 to 6 in number; borne both on the petiole and on the base of the blade.

Vegetative Buds:

*Size.*—Small.

*Shape.*—Ovoid, unless compressed between flower buds.

*Scales.*—Thick pubescence; moderate length.

*Color.*—Dark brown.

*Flowers*

Dates of first and full bloom: Over prolonged period of observation, varied from February 16 to February 25 for first bloom, and from February 24 to March 8 for full bloom, due to weather vrariations from year to year.

Dormant flower buds:

*Shape.*—Ovoid.

*Scales.*—Pubescent.

*Color.*—Dark brown, with pubescence giving a whitish effect.

Size (when fully open): Showy; medium size; about 1½ inches in diameter.

Petalage: Semi-double; usually from 10 to 14 petals.

Form: Cupped.

Color (open flower): Between Rose Pink, Plate 427/3, page 126 (Wilson) and Rose Pink, Plate 427/2, page 126 (Wilson), darkening with age generally toward near Spirea Red, Plate 025/3, page 112 (Wilson) and toward near Spirea Red, Plate 025/1, page 112 (Wilson) at point of attachment.

*Fruit*

Ripening dates: Generally ripens from early June to mid June at Wasco, California; over prolonged period of observation, the dates of first ripening ranged from June 5 to June 12; ripening dates ranged from a few days to a week after "June Gold" peach.

Maturity when described: Eating ripe.

Size: Somewhat variable, but generally medium size. Axial diameter—from 2¼ inches to 2⅝ inches. Transverse diameter in suture plane—from 2¼ inches to 2⅝ inches. Transverse diameter at right angles to suture plane—from 2¼ inches to 2½ inches.

Form: Relatively uniform; nearly symmetrical; from globose to broadly ovoid.

Suture: Generally shallow; extending from base to apex; slight depression beyond pistil point.

Ventral surface: Rounded; sometimes slightly lipped toward base and/or apex; rarely lipped throughout; sometimes not lipped at all.

Stem cavity: Somewhat rounded; elongated in suture plane, with suture showing on one side.

*Depth.*—From about ⅜ inch to about ½ inch.

*Width.*—From about 1 inch to about 1¼ inches.

*Markings.*—Usually distinct red streaks of varying width and length radiating from stem attachment opposite to suture.

Base: From rounded to truncate.

Apex: Short; apical pistil point.

Stem: Medium caliper; glabrous; from medium to weak adherence to stone. Length—about ½ inch.

Skin:

*Thickness.*—Medium.

*Texture.*—Medium.

*Tenacity to flesh.*—Free.

*Pubescence.*—From moderate to heavy; medium length.

*Color.*—Ground color varies from near Dresden Yellow, Plate 64/2, page 64 (Wilson) to near Maize Yellow, Plate 607/1, page 69 (Wilson), all lightly overlaid with flecks, streaks, mottling and blushes of from near Delft Rose, Plate 020/2, page 108 (Wilson) to near Rose Opal, Plate 022/1, page 110 (Wilson).

Flesh:

*Quality.*—Medium firm; melting; few tender fibres.

*Aroma.*—Pronounced.

*Flavor.*—Subacid.

*Color.*—Varies from near Saffron Yellow, Plate 7/3, page 7 (Wilson) to near Maize Yellow, Plate 607/1, page 69 (Wilson), with some small flecks of near Rose Madder, Plate 23/1, page 23 (Wilson); surface of pit cavity near Yellow Ochre, Plate 07, page 101 (Wilson), with some small flecks of near Rose Madder, Plate 23/1, page 23 (Wilson).

Stone:

*Tenacity of flesh.*—Free, but sometimes adheres to stone along ventral edge.

*Size.*—Medium. Length—about 1⅛ inches. Width—from ¾ inch to ⅞ inch. Thickness—from ⅝ inch to ¾ inch.

*Form.*—Ovoid; cuneate toward apex.

*Base.*—Somewhat oblique.

*Hilum.*—Narrow; oval to oblong.

*Apex.*—From rounded to acuminate.

*Sides.*—Slightly unequal; irregularly furrowed toward apex and sometimes near base; pitted from base to past center; sometimes pitted throughout.

*Ventral edge.*—Medium thickness; generally without wing.

*Dorsal edge.*—Narrow, shallow groove toward base; ridges on either side interrupted.

*Color.*—Between near Mikado Brown, Plate XXIX (Ridgway) and near Sayal Brown, Plate XXIX (Ridgway).

I claim:

A new and distinct variety of peach tree of the yellow-fleshed, freestone, fruit-bearing type, substantially as herein shown and described, characterized particularly as to novelty by the unique combination of a vigorous, compact, bushy, dwarf tree habit, with internodes of the stem averaging approximately ¼ inch in length, but bearing leaves of relatively normal or standard size and appearance which give the tree an attractive, bushy, densely foliaged appearance, while requiring little or no pruning to maintain its dwarf size, attractive, showy, semi-double pink flowers, a tree chilling requirement approximately equal to that of "Springtime" peach (Plant Patent No. 1,268), a habit of bearing heavy fruit crops under California conditions, with a habit of beginning to bear at a relatively early age, medium-sized fruit of good quality and flavor, said fruit being relatively uniform, nearly symmetrical and nearly round in shape, with the fruit having an attractive skin color of light yellow general color tonality, but moderately flecked, blushed and occasionally streaked with red, and a fruit ripening period averaging about early June in California, with the ripening period ranging from a few days to a week after that of "June Gold" peach (Plant Patent No. 1,884).

No references cited.